US00PP19353P2

(12) United States Plant Patent
Takeshita

(10) Patent No.: US PP19,353 P2
(45) Date of Patent: Oct. 21, 2008

(54) *CALIBRACHOA* PLANT NAMED 'KIRIFU-24'

(50) Latin Name: *Calibrachoa hybrida*
Varietal Denomination: Kirifu-24

(75) Inventor: Daigaku Takeshita, Tochigi-ken (JP)

(73) Assignee: Kirin Agriobio Co. Ltd., Tokyo (JP)

( * ) Notice: Subject to any disclaimer, the term of this patent is extended or adjusted under 35 U.S.C. 154(b) by 0 days.

(21) Appl. No.: 11/895,937

(22) Filed: Aug. 28, 2007

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Calibrachoa* plant named 'Kirifu-24' characterized by its outwardly spreading, mounding and trailing plant habit; vigorous growth habit; freely branching habit; early and freely flowering habit; small pale lavender-colored flowers; and good garden performance.

2 Drawing Sheets

Botanical designation: *Calibrachoa hybrida.*
Cultivar denomination: 'Kirifu-24'.

BACKGROUND OF THE INVENTION

The present invention relates to a new and distinct cultivar of *Calibrachoa,* botanically known as *Calibrachoa hybrida* and hereinafter referred to by the name 'Kirifu-24'.

The new *Calibrachoa* is a product of a planned breeding program conducted by the Inventor in Tochigi, Japan. The objective of the breeding program is to develop new uniform *Calibrachoa* cultivars with attractive flower coloration.

The new *Calibrachoa* originated from a cross-pollination made by the Inventor in May, 2001 in Tochigi, Japan of the *Calibrachoa pygmaea*×*Calibrachoa a parviflora* cultivar Kirifu Compact Blue, disclosed in U.S. Plant Pat. No. 14,134, as the female, or seed, parent with an unidentified property selection of *Calibrachoa pygmaea,* not patented, as the male, or pollen, parent. The new *Calibrachoa* was discovered and selected by the Inventor as a single flowering plant within the progeny of the stated cross-pollination in a controlled environment in Tochigi, Japan in September, 2001.

Asexual reproduction of the new *Calibrachoa* by terminal cuttings in a controlled environment in Tochigi, Japan since October, 2001, has shown that the unique features of this new *Calibrachoa* are stable and reproduced true to type in successive generations.

SUMMARY OF THE INVENTION

The cultivar Kirifu-24 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kirifu-24'. These characteristics in combination distinguish 'Kirifu-24' as a new and distinct cultivar of *Calibrachoa:*

1. Outwardly spreading, mounding and trailing plant habit.
2. Vigorous growth habit.
3. Freely branching habit.
4. Early and freely flowering habit.
5. Small pale lavender-colored flowers.
6. Good garden performance.

Plants of the new *Calibrachoa* can be compared to plants of the female parent, the cultivar Kirifu Compact Blue. Plants of the new *Calibrachoa* differ from plants of the cultivar Kirifu Compact Blue in the following characteristics:

1. Plants of the new *Calibrachoa* are larger than plants of the cultivar Kirifu Compact Blue.
2. Plants of the new *Calibrachoa* have larger flowers than plants of the cultivar Kirifu Compact Blue.
3. Plants of the new *Calibrachoa* flower earlier than plants of the cultivar Kirifu Compact Blue.

Plants of the new *Calibrachoa* can be compared to plants of the male parent selection. Plants of the new *Calibrachoa* differ from plants of the male parent selection in the following characteristics:

1. Plants of the new *Calibrachoa* are more vigorous and larger than plants of the male parent selection.
2. Plants of the new *Calibrachoa* are more trailing than and not as upright as plants of the male parent selection.
3. Plants of the new *Calibrachoa* and the male parent selection differ in flower color as plants of the male parent selection have creamy white-colored flowers.

Plants of the new *Calibrachoa* can also be compared to plants of the cultivar Kirifu Blue, disclosed in U.S. Plant Pat. No. 14,135. In side-by-side comparisons conducted in Tochigi, Japan, plants of the new *Calibrachoa* and the cultivar Kirifu Blue differed primarily in flower color.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa*.

The photograph on the first sheet comprises a side perspective view of a typical flowering plant of 'Kirifu-24' grown in a container.

The photograph on the second sheet comprises a close-up of a typical flower stem and leaves of 'Kirifu-24'.

DETAILED BOTANICAL DESCRIPTION

The aforementioned photographs and following observations, measurements and values describe plants grown in Santa Paula, Calif., under commercial practice during the spring in a polyethylene-covered greenhouse. During the production of the plants, day temperatures averaged 26° C., night temperatures averaged 12° C. and light levels ranged from 4,000 to 5,000 foot-candles. Plants had been growing for about three months when the photographs and description were taken. In the following description, color references are made to The Royal Horticultural Society Colour Chart, 1995 Edition, except where general terms of ordinary dictionary significance are used.

Botanical classification: *Calibrachoa hybrida* cultivar Kirifu-24.

Parentage:

*Female, or seed, parent.*—*Calibrachoa pygmaea*× *Calibrachoa parviflora* cultivar Kirifu Compact Blue, disclosed in U.S. Plant Pat. No. 14,134.

*Male, or pollen, parent.*—Unidentified propriety selection of *Calibrachoa pygmaea,* not patented.

Propagation:

*Type.*—By terminal cuttings.

*Time to initiate roots, summer.*—About three days at 27° C.

*Time to initiate roots, winter.*—About six days at 21° C.

*Time to produce a rooted young plant, summer.*—About three weeks at 27° C.

*Time to produce a rooted young plant, winter.*—About four weeks at 21° C.

*Root description.*—Fine, fibrous; white in color.

*Rooting habit.*—Freely branching; dense.

Plant description:

*Plant and growth habit.*—Outwardly spreading, mounding and trailing plant habit. Freely branching with about 20 lateral branches per plant. Vigorous growth habit.

*Plant height.*—About 10 cm.

*Plant diameter.*—About 26 cm.

Lateral branch description:

*Length.*—About 48 cm.

*Diameter.*—About 2.5 mm.

*Internode length.*—About 2.5 cm.

*Strength.*—Strong.

*Aspect.*—Initially upright to outwardly to decumbent.

*Texture.*—Pubescent; glandular.

*Color.*—146C.

Foliage description:

*Arrangement.*—Before flowering, alternate, simple; after flowering, opposite, simple; leaves sessile.

*Length.*—About 2.6 cm.

*Width.*—About 4 mm.

*Shape.*—Lanceolate to narrowly elliptic.

*Apex.*—Acute.

*Base.*—Attenuate.

*Margin.*—Entire.

*Texture, upper and lower surfaces.*—Pubescent; glandular.

*Venation pattern.*—Pinnate.

*Color.*—Developing foliage, upper and lower surfaces: 147B. Fully expanded foliage, upper surface: 146A; venation, 146B. Fully expanded foliage, lower surface: 146B; venation, 146B.

Flower description:

*Flower arrangement and habit.*—Single salverform flowers arising from upper leaf axils. Freely flowering habit with usually about 80 to 90 flowers developing per lateral branch. Flowers persistent. Flowers face upright or outwardly. Flowers not fragrant.

*Natural flowering season.*—Plants of the new *Calibrachoa* flower about nine weeks after planting. Long flowering period; flowering commences naturally during the spring and plants flower continuously until late autumn in Southern California.

*Flower longevity.*—Individual flowers last about seven to ten days on the plant.

*Flower diameter.*—About 1.5 cm.

*Flower length* (*depth*).—About 1 cm.

*Throat diameter.*—About 2 mm.

*Tube diameter.*—About 2 mm.

*Flower bud.*—Shape: Cylindrical. Length: About 1.2 cm. Diameter: About 4 mm. Color: 90B.

*Corolla.*—Arrangement: Five petals fused at the base and opening into a flared trumpet. Petal length from throat: About 7 mm. Petal width: About 6 mm. Petal shape: Spatulate. Petal apex: Cuspidate. Petal margin: Entire. Petal texture, upper and lower surfaces: Smooth, glabrous; velvety. Color: Petal, when opening, upper surface: 92B. Petal, when opening, lower surface: 90A. Petal, fully opened, upper surface: 91C; venation, 91B to 91C. Petal, fully opened, lower surface: 90B; venation, 89C. Throat: 145C; venation, 145B. Tube: 145A; venation, 147B.

*Calyx.*—Arrangement: One star-shaped calyx tube with five sepals fused at the base per flower. Sepal length: About 5 mm to 6 mm. Sepal width: About 1 mm. Sepal shape: Lanceolate. Sepal apex: Acute. Sepal base: Truncate. Sepal margin: Entire. Sepal texture, upper and lower surfaces: Pubescent. Color, upper and lower surfaces: 147B.

*Peduncles.*—Length: About 1 cm to 1.2 cm. Diameter: About 1 mm. Angle: Outwardly to curved upright. Strength: Strong. Texture: Pubescent. Color: 145C.

*Reproductive organs.*—Stamens: Quantity/arrangement: Five per flower. Anther shape: Oval. Anther length: About 1 mm. Anther color: 145A. Pollen amount: Scarce. Pollen color: 145A. Pistils: Quantity: One per flower. Pistil length: About 6 mm. Style length: About 4 mm. Style color: 145D. Stigma shape: Rounded. Stigma color: 146B. Ovary color: 145A. Seed/fruit: Seed and fruit development have not been observed on the plants of the new *Calibrachoa*.

Garden performance: Plants of the new *Calibrachoa* have been observed have good garden performance and to tolerate wind, rain and temperatures from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Kirifu-24' as illustrated and described.

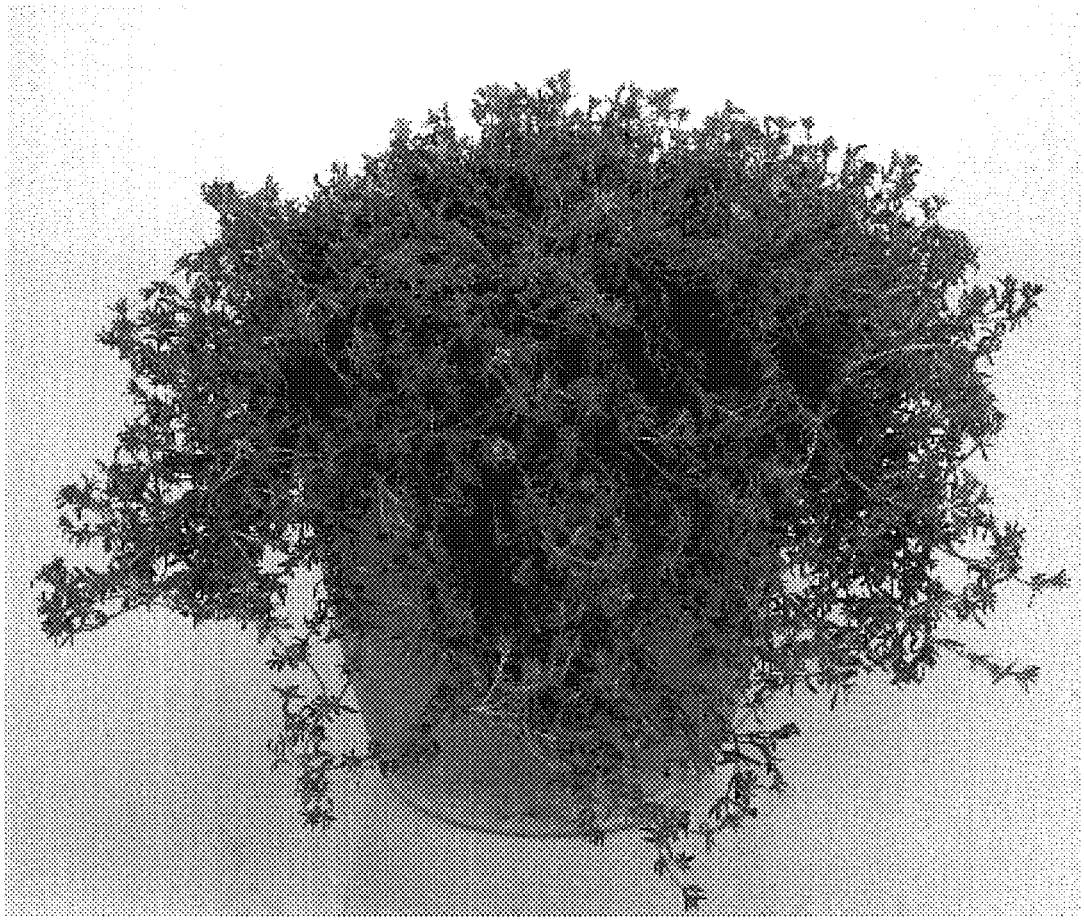

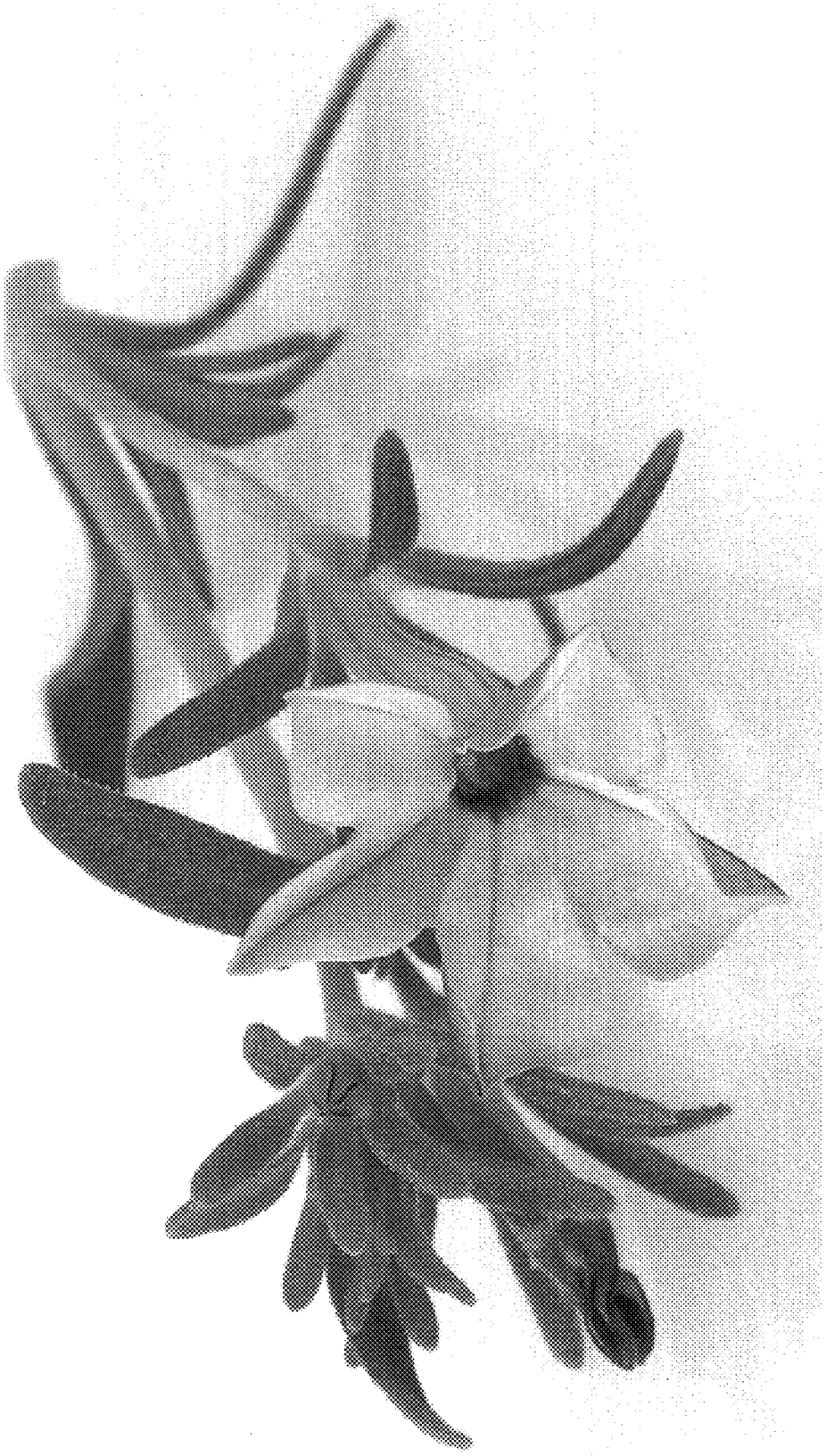

* * * * *